(12) United States Patent
Hillborg

(10) Patent No.: US 10,223,792 B2
(45) Date of Patent: Mar. 5, 2019

(54) SYSTEM AND METHOD FOR DETECTING BRAIN METASTASES

(71) Applicant: Elekta AB (Publ), Stockholm (SE)

(72) Inventor: Mikael Hillborg, Uppsala (SE)

(73) Assignee: ELEKTA AB (PUBL), Stockholm (SE)

(*) Notice: Subject to any disclaimer, the term of this patent is extended or adjusted under 35 U.S.C. 154(b) by 115 days.

(21) Appl. No.: 15/423,220

(22) Filed: Feb. 2, 2017

(65) Prior Publication Data
US 2018/0218501 A1    Aug. 2, 2018

(51) Int. Cl.
| | |
|---|---|
| *A61N 5/10* | (2006.01) |
| *G06K 9/46* | (2006.01) |
| *G06T 7/00* | (2017.01) |
| *G06T 7/11* | (2017.01) |
| *G06T 7/64* | (2017.01) |
| *G06T 7/70* | (2017.01) |
| *G06T 11/00* | (2006.01) |
| *G06K 9/00* | (2006.01) |

(52) U.S. Cl.
CPC ......... *G06T 7/0014* (2013.01); *A61N 5/1039* (2013.01); *A61N 5/1084* (2013.01); *G06K 9/4604* (2013.01); *G06T 7/11* (2017.01); *G06T 7/64* (2017.01); *G06T 7/70* (2017.01); *G06T 11/008* (2013.01); *G06K 2209/051* (2013.01); *G06T 2207/10081* (2013.01); *G06T 2207/10088* (2013.01); *G06T 2207/10132* (2013.01); *G06T 2207/20024* (2013.01); *G06T 2207/20036* (2013.01); *G06T 2207/30016* (2013.01); *G06T 2207/30096* (2013.01)

(58) Field of Classification Search
CPC .......................... G06K 9/0063; G06K 9/6857
USPC ....... 382/131, 128, 103, 132, 276, 291, 294, 382/133, 284; 705/3; 600/424; 435/6.12, 6.1, 501
See application file for complete search history.

(56) References Cited

U.S. PATENT DOCUMENTS

| | | | | |
|---|---|---|---|---|
| 2012/0178093 | A1* | 7/2012 | Weiss | C12Q 1/6886 435/6.12 |
| 2015/0371420 | A1* | 12/2015 | Yerushalmy | G06T 3/4038 382/284 |
| 2016/0070949 | A1* | 3/2016 | Tunstall | G06K 9/0014 382/133 |

* cited by examiner

*Primary Examiner* — Charlotte M Baker
(74) *Attorney, Agent, or Firm* — Finnegan, Henderson, Farabow, Garrett & Dunner, LLP

(57) ABSTRACT

The present disclosure provides systems, methods, and computer-readable storage media for detecting an anatomical region of interest for radiotherapy planning. Embodiments of the present disclosure may identify a plurality of objects in a medical image and select a subset of the objects by applying a morphology filter to the plurality of objects. The morphology filter may determine a morphological feature associated with each of the plurality of objects and exclude at least one object from the subset when the morphological feature of the at least one object exceeds a predetermined threshold. Embodiments of the present disclosure may also classify the objects in the subset into one of a predetermined set of shapes and detect the anatomical region of interest based on the classified objects in the subset.

27 Claims, 9 Drawing Sheets

SYSTEM AND METHOD FOR DETECTING BRAIN METASTASES

TECHNICAL FIELD

This disclosure relates generally to radiotherapy treatment planning. More specifically, this disclosure relates to systems and methods for detecting brain metastases in medical images for developing a radiotherapy treatment plan to be used during radiotherapy.

BACKGROUND

Radiotherapy is used to treat cancers and other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions and the like). The placement and dose of the radiation beam must be accurately controlled to ensure the tumor receives the prescribed radiation, and the placement of the beam should be such as to minimize damage to the surrounding healthy tissue.

Before administrating radiation doses to treat a patient, a treatment plan needs to be created, in which the manner of applying radiation doses are specified. A treatment plan is usually created based on a medical image (or a series of images) of the patient, in which an internal anatomical region of the patient is shown. From the medical image, the target to be treated is ascertained, as well as its location, size, and/or shape, based on which the directions and intensities of multiple radiation beams are determined such that the beams converge at the target location to provide the necessary radiation dose for treating the patient. While a physician may determine whether a particular object in the medical image is a target by visually observing the medical image, this process is often tedious and time consuming. Computer-aided image classification techniques can reduce the time to extract some or all required information from the medical image.

For example, some methods rely on training data to train a statistical model, and the trained statistical model may then be used to identify a target. However, the effectiveness of such methods depends largely on the quality of the training data. In order to obtain acceptable results, the training data have to contain accurately identified targets in terms of their location and segmentation. Usually, such high quality training data are in short supply.

In another example, pure image processing methods have been used to enhance the visibility of the medical image to allow the physician to better observe the medical image. Such methods, however, lack the classification ability to determine whether a particular object in the medical image is a target or not.

The present disclosure is directed to overcoming or mitigating one or more of these problems set forth.

SUMMARY

One aspect of the present disclosure relates to a system for detecting an anatomical region of interest. The system may include a memory device storing computer-executable instructions and at least one processor device communicatively coupled to the memory device. The computer-executable instructions, when executed by the at least one processor device, cause the processor device to perform various operations. The operations may include identifying a plurality of objects in a medical image. The operations may also include selecting a subset of the objects by applying a morphology filter to the plurality of objects. The morphology filter may determine a morphological feature associated with each of the plurality of objects and exclude at least one object from the subset when the morphological feature of the at least one object exceeds a predetermined threshold. The operations may also include classifying the objects in the subset into one of a predetermined set of shapes. Moreover, the operations may include detecting the anatomical region of interest based on the classified objects in the subset.

Another aspect of the present disclosure relates to a method for detecting an anatomical region of interest. The method may be implemented by at least one processor device executing computer-executable instructions. The method may include identifying a plurality of objects in a medical image. The method may also include selecting a subset of the objects by applying a morphology filter to the plurality of objects. The morphology filter may determine a morphological feature associated with each of the plurality of objects and exclude at least one object from the subset when the morphological feature of the at least one object exceeds a predetermined threshold. The method may also include classifying the objects in the subset into one of a predetermined set of shapes. Moreover, the method may include detecting the anatomical region of interest based on the classified objects in the subset.

A further aspect of the present disclosure relates to a non-transitory computer-readable medium that stores a set of instructions that is executable by at least one processor of a device to cause the device to perform a method for detecting an anatomical region of interest. The method may include identifying a plurality of objects in a medical image. The method may also include selecting a subset of the objects by applying a morphology filter to the plurality of objects. The morphology filter may determine a morphological feature associated with each of the plurality of objects and exclude at least one object from the subset when the morphological feature of the at least one object exceeds a predetermined threshold. The method may also include classifying the objects in the subset into one of a predetermined set of shapes. Moreover, the method may include detecting the anatomical region of interest based on the classified objects in the subset.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts.

Systems and methods consistent with the present disclosure are directed to detecting an anatomical region of interest in a medical image (or a series of medical images) for developing a radiotherapy treatment plan. The anatomical region of interest may include a tumor, a cancer, an organ at risk, etc. In some embodiments, the anatomical region of interest may include a brain metastasis. An anatomical region of interest may also be referred to as a target. As used herein, the term "anatomical region of interest" is interchangeable with the term "target." Detection of a target may include one or more of the following aspect: (1) classification or identification, indicating whether a target is present in the medical image or whether a particular object shown in the medical image is a target; (2) positioning, indicating the position or location of the target, once identified, in two-dimensional (2D) and/or three-dimensional (3D) space; and (3) outlining or segmentation, indicating one or more ways of separating, emphasizing, or differentiating the identified target from other features or the background of the medical image.

For example, an object shown in the medical image may be classified/identified as a target in a binary manner: is a target or is not a target. In another example, the classification/identification may be carried out based on probability or likelihood. In some embodiments, an object may be identified as being, for example, highly likely a target, indicating a high probability that the object is in fact a target. Similarly, an object may be identified as being less likely a target. The probability or likelihood associated with an classification or identification may be described by a confidence measure, such as a percentage number, to quantify the probability or likelihood.

The spatial location may be indicated by the (X, Y, Z) coordinates of the target in a Cartesian system, or other appropriate coordinates if other spatial coordinate systems (e.g., cylindrical, spherical, etc.) are used.

Various methods may be used to outline or segment a target. For example, the target may be outlined by a contour surrounding the target. In another example, the target may be rendered in a different color from the background or other features shown in the medical image. It would be apparent to a person skilled in the art to use other appropriate methods to separate, emphasize, or differentiate the identified target.

The medical image(s) may include images generated from various imaging modalities. For example, the medical image(s) may include a Magnetic Resonance Imaging (MRI) image, a computed tomography (CT) image, an ultrasound image, or the like. The medical image(s) may be 2D or 3D. A 3D image may include a plurality of 2D slices.

A certain kind of target to be detected may have one or more morphology features that are specific to that kind of target. For example, most brain metastases are round in shape. Such morphology features may provide useful information to the detection of the corresponding kind of target and may lead to improved efficiency and accuracy. Embodiments of the present disclosure provide exemplary systems and methods that utilize such morphology features in the detection of targets such as brain metastases. The detection result may be used to develop a treatment plan for conducting radiotherapy treatment.

Figure 1:
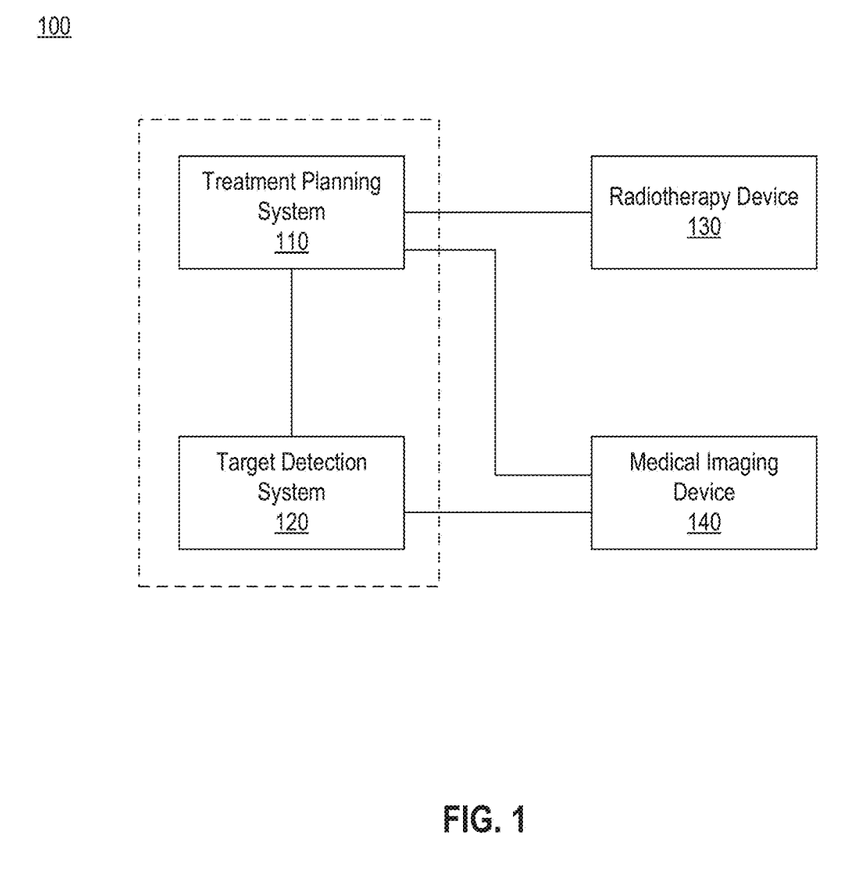
FIG. 1 illustrates an exemplary radiotherapy system including a target detection system, according to some embodiments of the present disclosure.

FIG. 1 illustrates an exemplary radiotherapy system 100, according to some embodiments of the present disclosure. Radiotherapy system 100 may include a treatment planning system 110, a target detection system 120, a radiotherapy device 130, and a medical imaging device 140. In addition, radiotherapy system 100 may include a display device and a user interface (not shown).

As shown in FIG. 1, target detection system 120 may communicate with medical imaging device 140 to receive one or more medical images. Target detection system 120 may detect one or more targets in the medical image(s) and communicate the detection result with treatment planning system 110. Treatment planning system 110 may provide a treatment plan based, at least partially, on the detection result, and communicate the treatment plan with radiotherapy device 130. Treatment planning system may also communicate with medical imaging device 140 to receive medical images directly, such as updated medical image(s) before or during the treatment process. During the treatment, radiotherapy device 130 may administer radiation doses to a patient according to the treatment plan.

In some embodiments, radiotherapy device 130 may be local with respect to treatment planning system 110. For example, radiotherapy device 130 and treatment planning system 110 may be located in the same room of a medical facility/clinic. In other embodiments, radiotherapy device 130 may be remote with respect to treatment planning system 110 and the data communication between radiotherapy device 130 and treatment planning system 110 may be carried out through a network (e.g., a local area network (LAN); a wireless network; a cloud computing environment such as software as a service, platform as a service, infrastructure as a service; a client-server; a wide area network (WAN); or the like). Similarly, the communication links between target detection system 120 and treatment planning system 110, between target detection system 120 and medical imaging device 140, and between treatment planning system 110 and medical imaging device 140, may also be implemented in a local or remote manner.

In some embodiments, treatment planning system 110 and target detection system 120 may be implemented in a single data processing device, as indicated by the dashed line box in FIG. 1. For example, treatment planning system 110 and target detection system 120 may be implemented as different software programs operating on the same hardware device. In other embodiments, treatment planning system 110 and target detection system 120 may be implemented using different data processing devices.

Medical imaging device 140 may include an MRI imaging device, a CT imaging device, an X-ray imaging device, a positron emission tomography (PET) imaging device, an ultrasound imaging device, a fluoroscopic device, a single-photo emission computed tomography (SPECT) imaging device, or other medical imaging devices for obtaining one or more medical images of a patient. Accordingly, medical imaging device 140 may provide various kinds of medical images. For example, the medical images may include MRI images, CT images, PET images, X-ray images, ultrasound images, SPECT images, etc.

Figure 2A:
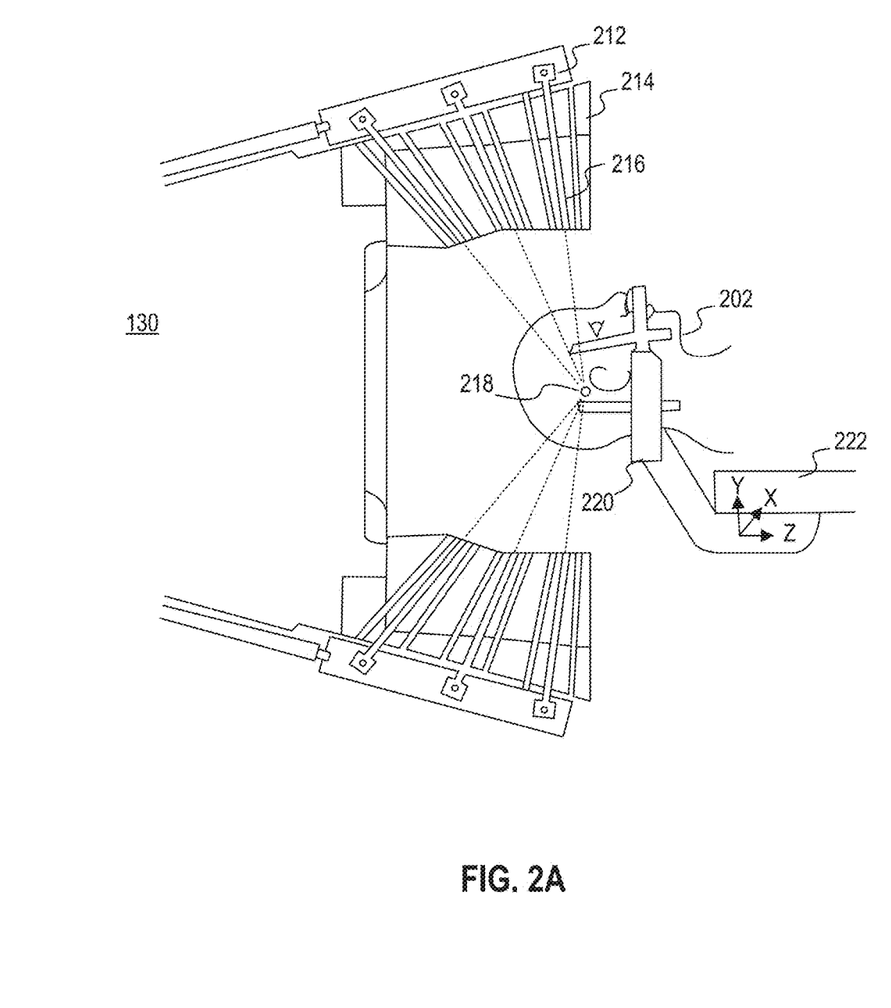
FIG. 2A illustrates an exemplary radiotherapy device, a Gamma Knife, according to some embodiments of the present disclosure.

FIG. 2A illustrates an example of one type of radiotherapy device 130 (e.g., Leksell Gamma Knife), according to some embodiments of the present disclosure. As shown in FIG. 2A, in a radiotherapy treatment session, a patient 202 may wear a coordinate frame 220 to keep stable the patient's body part (e.g., the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212. Radiation sources 212 may generate a plurality of radiation beams (e.g., beam lets) through beam channels 216. The plurality of radiation beams may be configured to focus on an isocenter 218 from different directions. While each individual radiation beam may have a relatively low intensity, isocenter 218 may receive a relatively high level of radiation when multiple doses from different radiation beams accumulate at isocenter 218. In some embodiments, isocenter 218 may correspond to a target under surgery or treatment, such as a tumor.

Figure 2B:
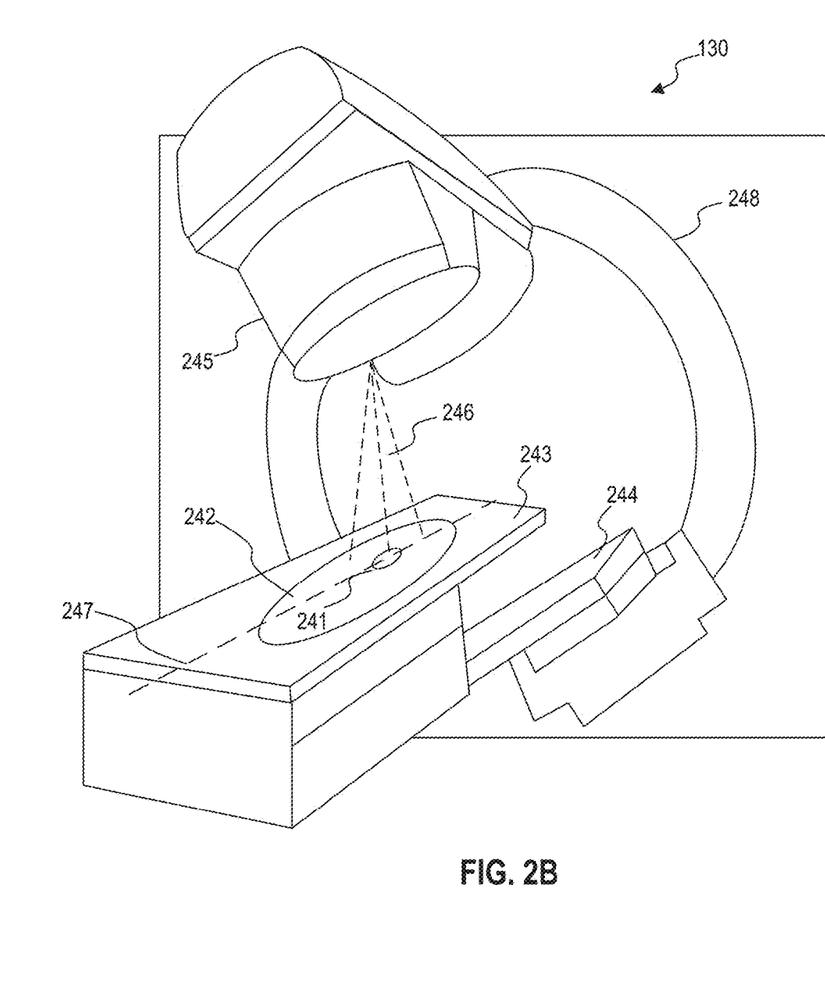
FIG. 2B illustrates another examplary radiotherapy device, a linear accelerator (LINAC), according to some embodiments of the present disclosure.

FIG. 2B illustrates another example of radiotherapy device 130 (e.g., a linear accelerator), according to some embodiments of the present disclosure. Using a linear accelerator, a patient 242 may be positioned on a patient table 243 to receive the radiation dose according to the treatment plan. Linear accelerator 130 may include a radiation head 245 that generates a radiation beam 46. Radiation head 245 may be rotatable around a horizontal axis 247. In addition, below the patient table 243 there may be provided a flat panel scintillator detector 244, which may rotate synchronously with radiation head 245 around an isocenter 241. The intersection of axis 247 with the center of beam 246, produced by radiation head 245, is usually referred to as the "isocenter." Patient table 243 may be motorized so that patient 242 can be positioned with the tumor site at or close to the isocenter 241. Radiation head 245 may rotate about a gantry 248 to provide patient 242 with a plurality of varying dosages of radiation according to the treatment plan.

Figure 3:
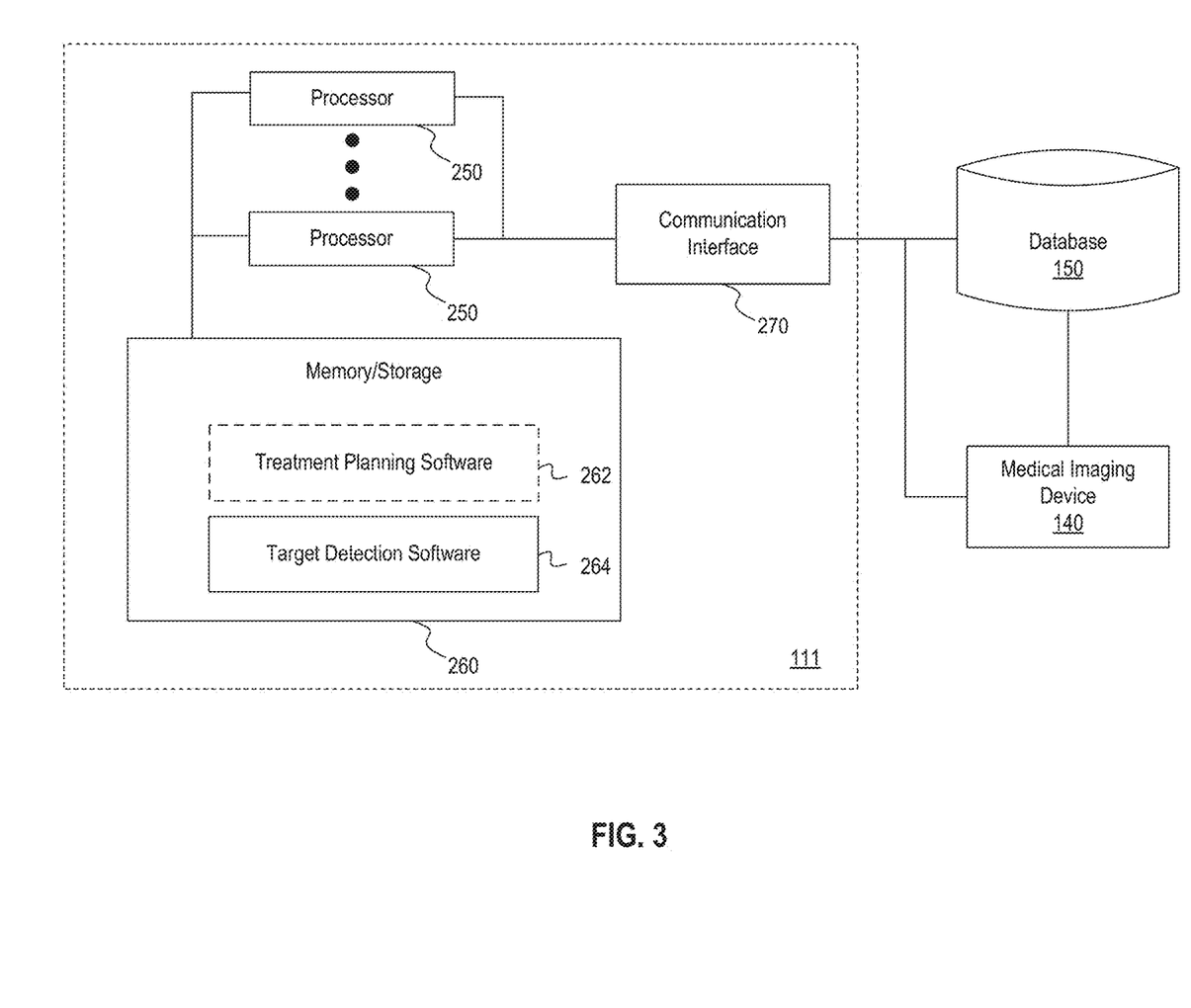
FIG. 3 illustrates an exemplary data processing device implementing the target detection system of FIG. 1, according to some embodiments of the present disclosure.

FIG. 3 illustrates an embodiment of a data processing device 111. Data processing device 111 may implement target detection system 120, treatment planning system 110, or both. As shown in FIG. 3, data processing device 111 may include one or more processors 250, a memory or storage device 260, and a communication interface 270. Memory/storage device 260 may store computer-executable instructions, such as target detection software 264. Memory/storage device 260 may optionally store treatment planning software 262.

Processor 250 may include one or more processor units, or a single processor unit with one or more cores. As used herein, a "computing core" of processor 250 may refer to either a processor unit or a core of a processor unit that is capable of executing instructions in a parallel-computing manner. For example, a computation task may be partitioned into multiple parallel branches or "threads," each branch/thread may be executed by a computing core in parallel with other computing core(s).

Processor 250 may be communicatively coupled to memory/storage device 260 and configured to execute the computer executable instructions stored thereon. For example, processor 250 may execute target detection software 264 to implement functionalities of target detection system 120. Optionally, processor device 250 may execute treatment planning software 262 (e.g., such as Monaco® software manufactured by Elekta) that may interface with target detection software 264.

Processor 250 may communicate with a database 150 through communication interface 270 to send/receive data to/from database 150. Database 150 may communicate with medical imaging device 140 and store medical image data obtained by medical imaging device 140. Database 150 may include a plurality of devices located either in a central or distributed manner. Processor 250 may also communicate with medical imaging device 140 directly through communication interface 270.

Processor 250 may include one or more general-purpose processing devices such as a microprocessor, a central processing unit (CPU), a graphics processing unit (GPU), or the like. More particularly, processor 250 may include a complex instruction set computing (CISC) microprocessor, a reduced instruction set computing (RISC) microprocessor, a very long instruction word (VLIW) microprocessor, a processor implementing other instruction sets, or a processor implementing a combination of instruction sets. Processor 250 may also include one or more special-purpose processing devices such as an application specific integrated circuit (ASIC), a field programmable gate array (FPGA), a digital signal processor (DSP), a system on a chip (SoC), or the like.

Memory/storage device 260 may include a read-only memory (ROM), a flash memory, a random access memory (RAM), a static memory, a flash memory, a hard drive, etc. In some embodiments, memory/storage device 260 may include a computer-readable medium. While the computer-readable medium in an embodiment may be a single medium, the term "computer-readable medium" should be taken to include a single medium or multiple media (e.g., a centralized or distributed database, and/or associated caches and servers) that store the one or more sets of computer-executable instructions or data. The term "computer-readable medium" shall also be taken to include any medium that is capable of storing or encoding a set of instructions for execution by a computer and that cause the computer to perform any one or more of the methodologies of the present disclosure. The term "computer readable medium" should accordingly be taken to include, but not be limited to, solid-state memories, optical, and magnetic media.

Communication interface 270 may include a network adaptor, a cable connector, a serial connector, a USB connector, a parallel connector, a high-speed data transmission adaptor such as fiber, USB 3.0, thunderbolt, and the like, a wireless network adaptor such as a WiFi adaptor, a telecommunication (3G, 4G, LTE and the like) adaptor, and the like. Communication interface 270 may provide the functionality of a local area network (LAN), a wireless network, a cloud computing environment (e.g., software as a service, platform as a service, infrastructure as a service, etc), a client-server, a wide area network (WAN), and the like. Processor 250 may communicate with database 150 and medical imaging device 140 via communication interface 270.

Radiotherapy treatment planning may require detection or delineation of a target, such as a tumor, an OAR, or healthy tissue surrounding the tumor or in close proximity to the tumor. As discussed above, classification, positioning, and segmentation of the target may be performed to allow study of the dose distribution in or around the target.

Figure 4:
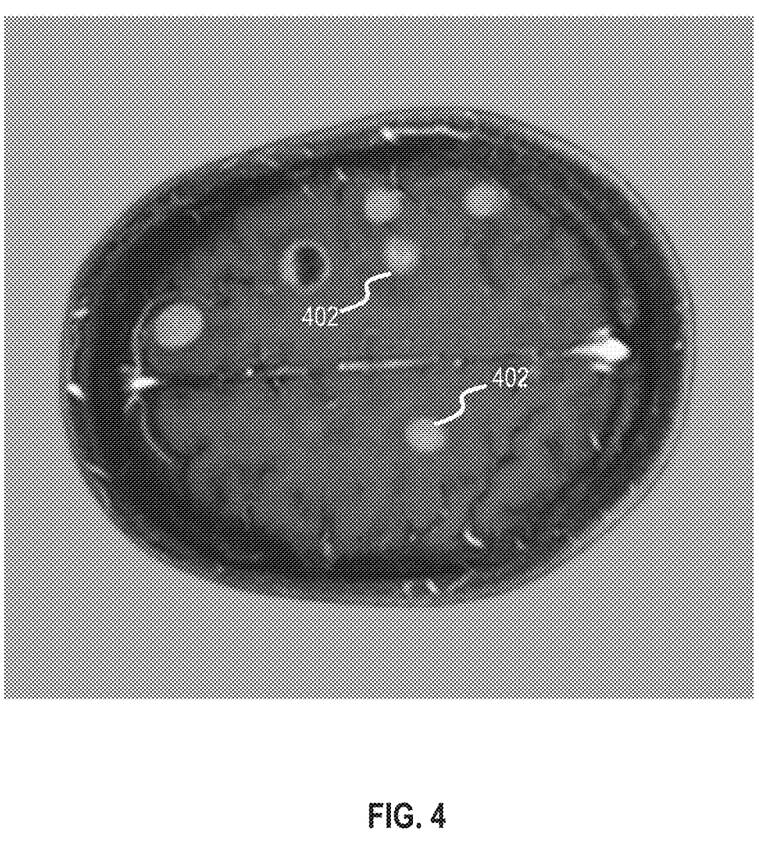
FIG. 4 is an exemplary medical image showing brain metastases.

During target detection, one or more medical images, such as MRI images, CT images, PET images, fMRI images, X-ray images, ultrasound images, radiotherapy portal images, SPECT images and the like, of the patient undergoing radiotherapy may be obtained by medical imaging device 140 to reveal the internal structure of a body part. FIG. 4 shows an exemplary medical image of a patient's brain, in which several brain metastases are shown as white rounded objects 402. After one or more objects in the medical image(s) are identified as target(s), segmentation may be carried out. For example, a 3D structure of one or more identified targets may be generated. The 3D structure may be obtained by contouring the target within each 2D layer or slice of an MRI or CT image and combining the contours of multiple 2D layers or slices. The contours may be generated manually (e.g., by a physician, dosimetrist, or health care worker) or automatically (e.g., using a program such as the Atlas-based Autosegmentation software, ABAS®, manufactured by Elekta).

Embodiments of the present disclosure may perform automatic classification, segmentation, and positioning of a target from one or more medical images based on morphological feature(s) of the target being detected. An exemplary work flow using target detection system 120 to detect one or more targets in a medical image is shown in FIG. 5.

Figure 5:
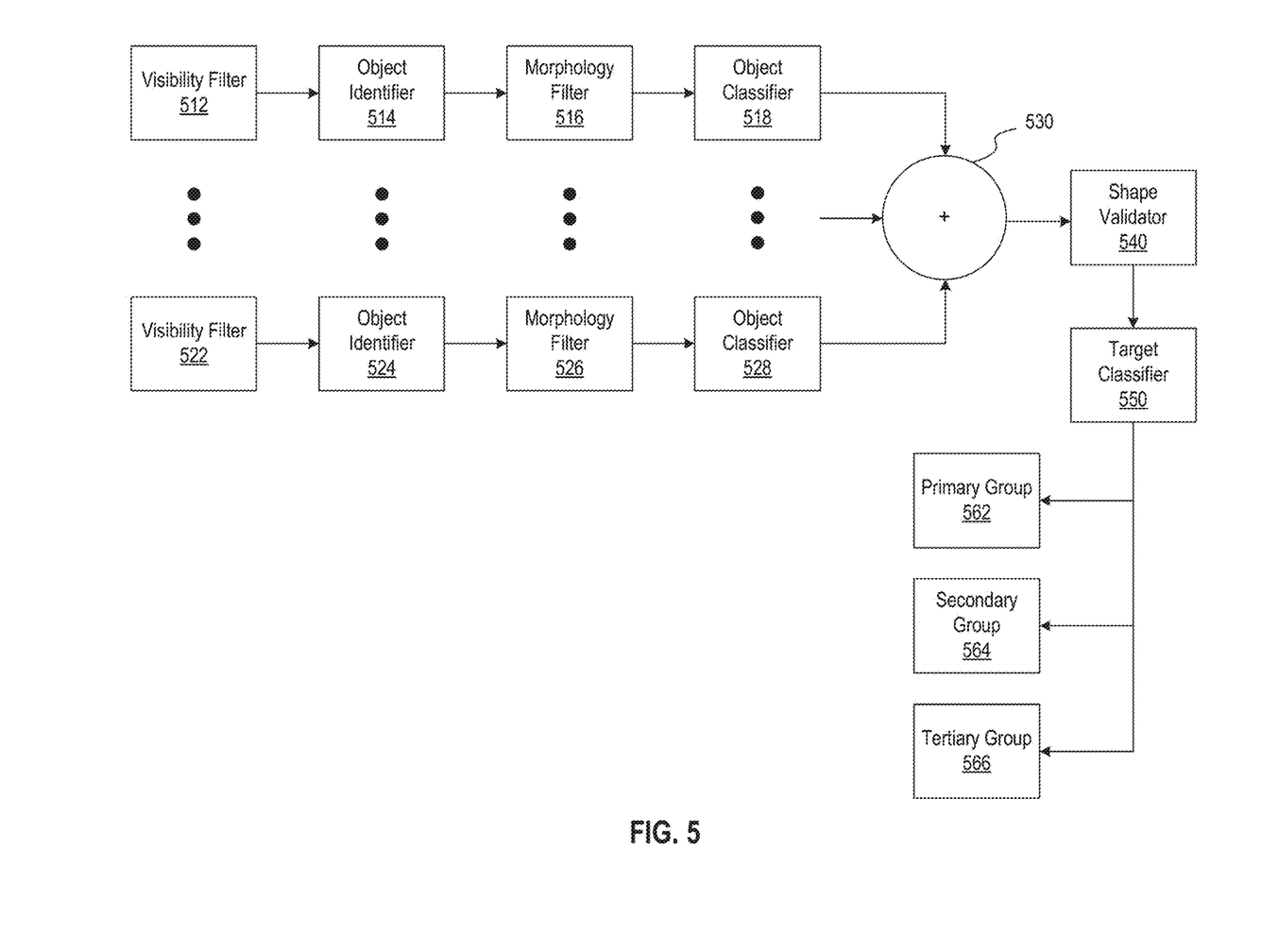
FIG. 5 is a block diagram showing exemplary components of the target detection system of FIG. 1, according to some embodiments of the present disclosure.

Referring to FIG. 5, target detection system 120 may include components forming one or more operational branches that can be executed in parallel. For example, one such branch includes a visibility filter 512, an object identifier 514, a morphology filter 516, and an object classifier 518. A parallel branch includes similar components 522, 524, 526, and 528. In some embodiments, target detection system 120 may receive a 3D medical image including a plurality of 2D slices, and each 2D slice may be processed by a respective branch. In this way, multiple 2D slices may be processed in parallel, increasing the processing speed. In some embodiments, one or more 2D medical images may also be processed by a single branch in series (e.g., for debugging or review purposes). In the following, detail functions of each component shown in FIG. 5 will be described in the context of detecting a brain metastasis target in a 3D MRI image. Other types of target in other types of medical images may be similarly detected.

As discussed above, a 3D MRI image may include a plurality of 2D slices, and each slice may correspond to an X-Y plane at a fixed Z coordinate. Each 2D slice may be separately processed by a branch to achieve parallel processing. In each branch, for example the branch including 512, 514, 516, and 518, a medical image (e.g., a 2D slice) may first undergo a pre-processing stage in which visibility filter 512 can enhance the visibility of the medical image. For example, visibility filter 512 may include an anisotropic diffusion filter to reduce noise in the medical image without removing significant features such as edges, lines, or other relevant information for detecting brain metastases. Visibility filter 512 may also include an intensity thresholding filter to remove most background noise through an adaptive/auto contrast processing. Visibility filter 512 may also include a grey level filter to quantize the grey level of the medical image. One or more of the above filters may be used to pre-process the medical image.

After pre-processing, object identifier 514 may identify one or more objects in the medical image. The objects may include any shape that appears to be different from the background in the medical image. Object identifier 514 may further find the contour of each identified object. The contour may enclose part of or the entire region of the object. An object may also be identified by its corresponding contour.

After one or more objects and their contours have been identified, the medical image may be processed by morphology filter 516 to remove any object that is likely not a brain metastasis. As described above, a certain type of target may have a target-specific morphological feature that can be used to differentiate that particular type of target from others. For example, most brain metastases resemble a roundish shape. Therefore, if an object is not in a round shape or close to the round shape, that object is likely not a brain metastasis. Therefore, morphology filter 516 may exclude one or more objects identified by object identifier 514 based on the shape of these objects. For example, morphology filter 516 may determine a depth of a convexity defect found in an object to evaluate the shape of that object.

Figure 6:
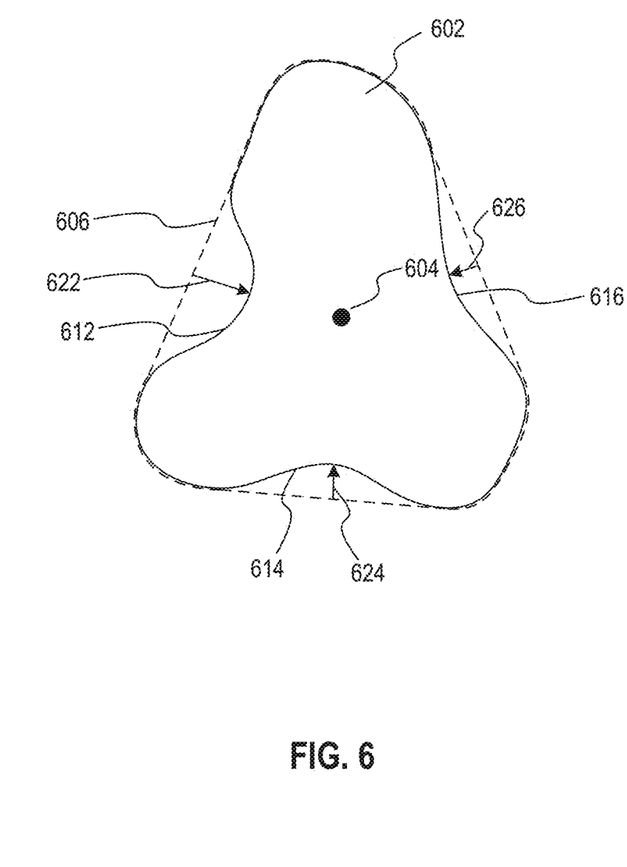
FIG. 6 schematically illustrates an object having convexity defects.

FIG. 6 shows a schematic representation of an object having convexity defects. Referring to FIG. 6, object 602 may be one that has been identified by object identifier 514, with an identified contour shown in a solid line enclosing the object. To evaluate the shape of object 602, morphology filter 516 may first determine a convex hull 606 enclosing object 602, shown as a dashed-line enclosure in FIG. 6. Convex hull 606, as shown in FIG. 6, may be visualized as a "rubber band" stretched around object 602 as a shape envelope. Morphology filter 516 may then determine all convexity defects in the contour of object 602. For example, the contour of object 602 has three convexity defects 612, 614, and 616, indicating portions of the contour extending inward from convex hull 606. For each convexity defect, morphology filter 516 may determine the depth of the convexity defect, such as depths 622, 624, and 626. For example, the depth may be determined based on a distance from the convexity defect to the convex hull. In some embodiment, the distance may be measured from convex hull 606 to the deepest point inwards the center (604) of objet 602. Morphology filter 516 may compare all depths and use the depth of the deepest convexity defect (e.g., 622) as an indicator of the roundishness (or non-roundishness) of object 602.

In addition to the convexity defect, morphology filter 516 may determine other shape related factors. For example, morphology filter 516 may determine a rectangle surrounding an object/contour, and determine the area of the rectangle. Then, morphology filter 516 may determine the area occupied by the object, and determine a ratio between the area occupied by the object and the area of the rectangle. In another example, morphology filter 516 may determine the height and width of the convex hull and determine a ratio between the height and the width. In a further example, morphology filter 516 may determine the number of convexity defects, the number of turns when moving along the contour of the object, etc. All these factors may be used to evaluate the shape of the object, for example, determine whether the object is roundish enough. If not, then the object may be excluded from a subset of candidate objects that are subject to further classification. For example, if the depth of the deepest convexity defect found in an object exceeds a predetermined threshold, then morphology filter 516 may determine that the object is likely not a brain metastasis. The object may then be excluded from the candidate subset for classification purposes. In some embodiments, the object may be removed from the medical image by, for example, flood filling the area enclosed by the contour of the object using the background color. In some embodiments, morphology filter 516 may exclude contour(s) of the skull from the candidate subset.

Referring back to FIG. 5, morphology filter 516 may exclude, for example, as many objects as possible from the candidate subset based on the morphological feature associated with the target subject to classification. In this way, morphology filter 516 effectively reduces the number of objects that need to be further processed. Therefore, morphology filter 516 may also be viewed as selecting the candidate subset (e.g., object(s) that are still remain after the filtering) from all of the objects identified by object identifier 514. The object(s) in the selected candidate subset may be classified by object classifier 518. In some embodiments, object classifier 518 may classify the objects into a predetermined set of shapes, such as points, lines, rounds, and complex shapes. The object(s)/contour(s) in the candidate subset, as well as their respective shape(s) as classified by object classifier 518 may be stored for further processing.

After all branches finish processing their respective 2D slices, the processing results may be combined by an adder 530. For example, all of the 2D slices may be stacked together in the original order (e.g., along the Z axis). Adder 530 may merge adjacent contours (e.g., adjacent along the Z axis across multiple 2D slices) into a single contour. The processing result obtained from each 2D slice may be validated in a 3D context by shape validator 540. Shape validator 540 may further remove or exclude object(s) from a collection of candidate subsets resulting from the processing conducted by the one or more branches. For example, shape validator 540 may remove objects classified as points or lines, leaving only those objects classified as rounds and complex shapes. In another example, shape validator 540 may remove all non-circular shapes from their respective subsets. In a further example, shape validator 540 may remove one or more objects classified as non-circular shapes from their respective subsets when the respective subsets do not include any object classified as the round shape. Depending on the desired recall rate (e.g., likelihood of missing a true target), the removal of objects based on their classified shape type may be made more inclusive (e.g., removing less objects) or more exclusive (e.g., removing more objects). The particular choice may depend on the balance between efficiency and recall rate.

Shape validator 540 may also remove an object from its respective subset when the object is not adjacent to another object located in an adjacent 2D slice. For example, a brain metastasis, being a roundish object, normally will show in multiple adjacent 2D slices that are located next to each other along the Z axis, and these adjacent objects may be merged by adder 530, as described above. If an object is isolated in a single 2D slice without adjacent counterparts shown in adjacent slices, it is likely that the object is not a brain metastasis.

Shape validator 540 may also remove a pair of objects mirroring each other from their respective subsets. These mirroring objects are likely ordinary brain structures, not brain metastases.

Shape validator 540 may also remove one or more objects located at a predetermined anatomical area from their respective subsets. For example, objects located along the horizontal middle blood vessel are likely not brain metastases.

After further removal of objects by shape validator 540, the remaining objects in the collection of subsets may be passed to target classifier 550 for classification. Target classifier 550 may evaluate the factors determined for each object in previous processing and determine a confidence measure for each of the remaining object. The confidence measure may indicate a likelihood that a particular object is a brain metastasis. For example, the confidence measure may be determined based on the degree of roundishness, the depth of any convex defect, the number of convex defects, the ratio between the area occupied by the object and the area of the rectangle enclosing the object, the ratio between the height of the convex hull and the width of the convex hull, etc.

Target classifier 550 may divide the remaining objects into a plurality of groups based on their respective confidence measures. For example, objects having high confidence measures, indicating that the objects are highly likely brain metastases, may be placed in a primary group 562. Similarly, objects having lower confidence measures may be placed in a secondary group 564, and objects having even lower confidence measures, but still maybe brain metastases may be placed in a tertiary group 566. Each object may be outlined by a contour and may be displayed to a user.

Figure 7:
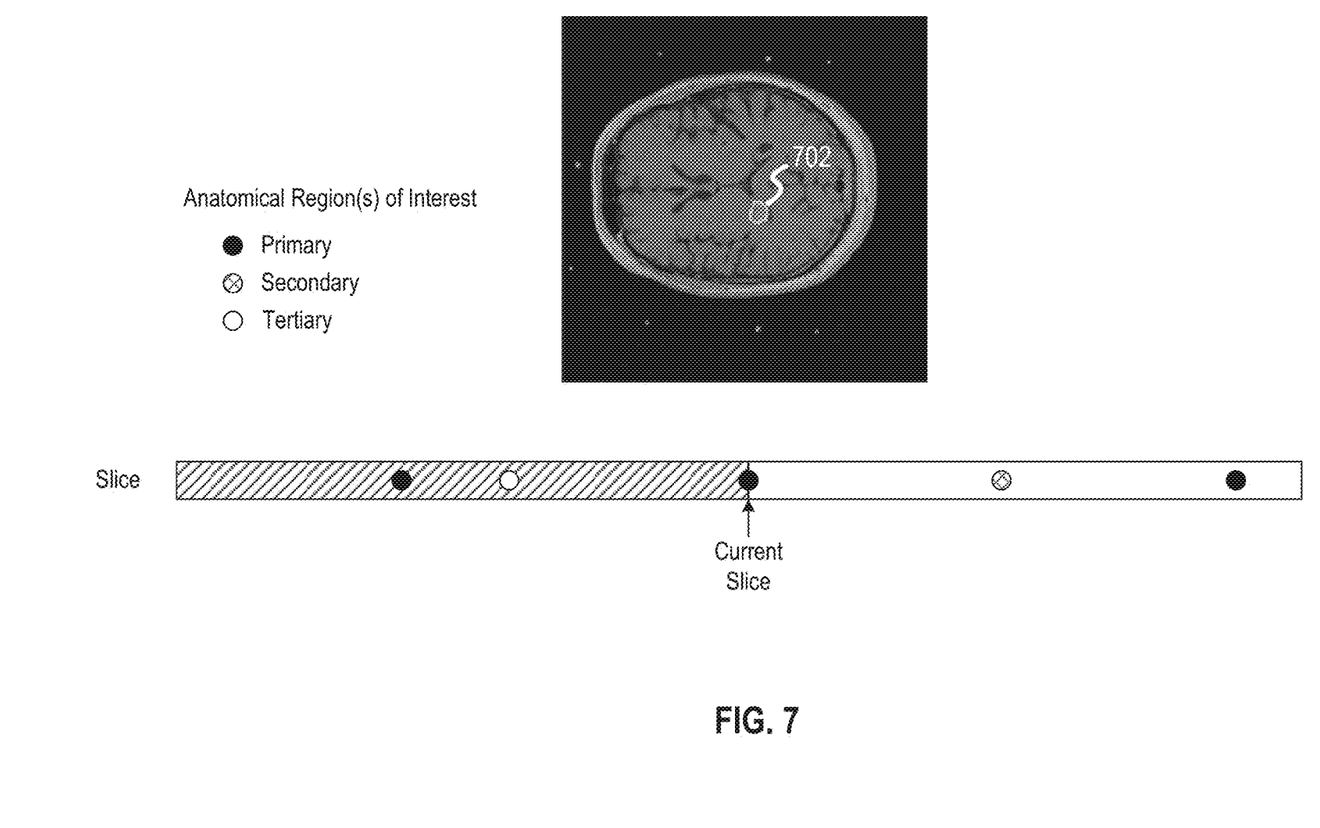
FIG. 7 shows an exemplary output of the target detection system shown in FIG. 1.

FIG. 7 shows an exemplary output of target detection system 120. As shown in FIG. 7, a 2D slice of an MRI image of a patient's brain is shown in the center. The image includes a classified target 702 outlined by a highlighted contour. A bar under the image indicates the slice position in the 3D slice deck (e.g., along the Z axis) and the position of the slice(s) in which a target is found. As indicated by the legends on the left, a solid circle means that the 2D slice at the indicated position includes a target in the primary group, a shadowed circle means that the 2D slice at the indicated position includes a target in the secondary group, and a white circle means that the 2D slice at the indicated position includes a target in the tertiary group. A user may choose a particular position on the slice bar to view the corresponding slice. When the chosen slice includes a classified target, the target is shown by a highlighted contour.

After the target have been detected, a dosimetrist, physician or healthcare worker may determine a dose of radiation to be applied to the target and any other anatomical structures proximate to the target. After the dose is determined for each anatomical structure (e.g., tumor, OAR, etc.), a process known as inverse planning may be performed to determine one or more plan parameters, such as volume delineation (e.g., define target volumes, contour sensitive structures), margins around the tumor and OARs, dose constraints (e.g., full dose to the tumor and zero dose to any OAR; 95% of dose to PTV while spinal cord ≤45 Gy, brain stem ≤55 Gy, and optic structures <54 Gy, etc.), beam angle selection, collimator settings, and beam-on times. The result of inverse planning may constitute a radiotherapy treatment plan that may be stored in treatment planning system 110. Radiotherapy device 130 may then use the generated treatment plan having these parameters to deliver radiotherapy to a patient.

Figure 8:
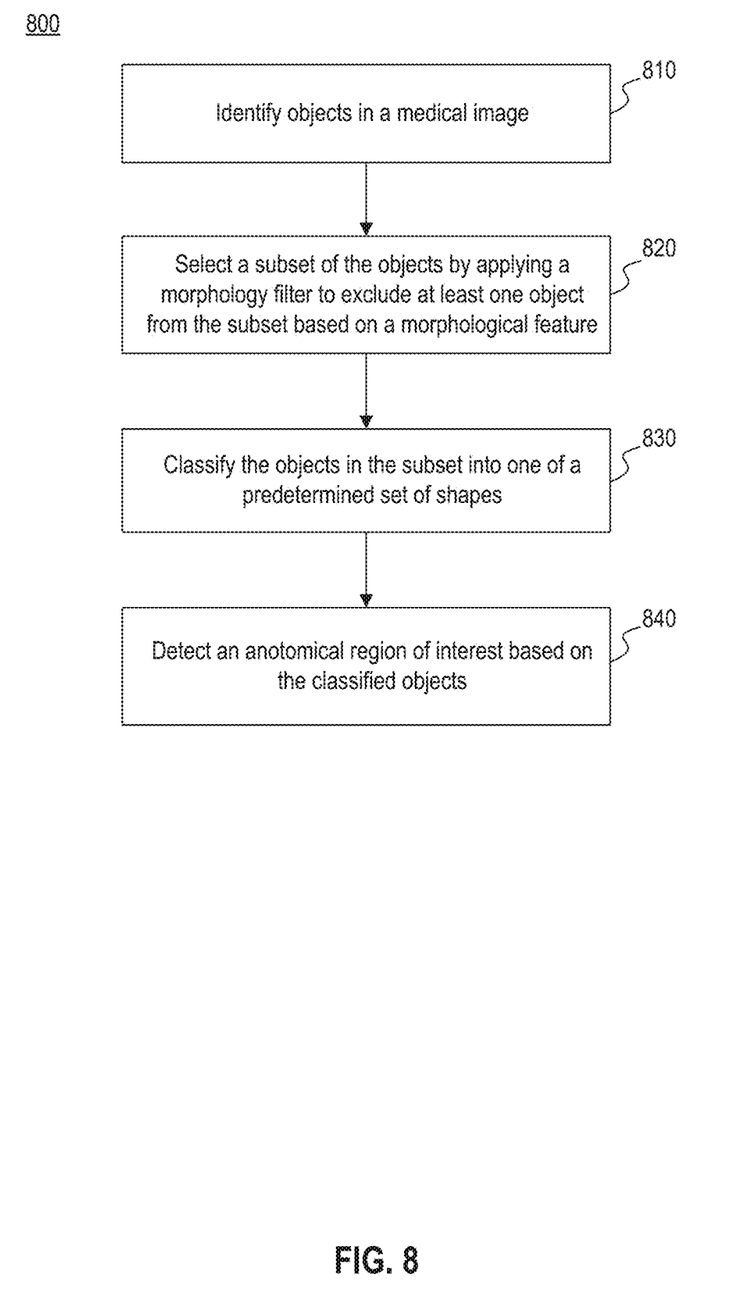
FIG. 8 is a flowchart illustrating an exemplary method for detecting a target, according to some embodiments of the present disclosure.

FIG. 8 is a flowchart illustrating an exemplary method 800 for detecting a target. In step 810, object identifier 514 may identify a plurality of objects in a medical image (e.g., an MRI image). In step 820, morphology filter 516 may select a subset of the objects based on a morphological feature (e.g., a depth of a convexity defect). For example, morphology filter 516 may exclude an object from the subset when the depth of a deepest convexity defect found on the object exceeds a predetermined threshold. In step 830, object classifier 518 may classify the objects in the subset into one of a predetermined set of shapes, such as the shapes of point, line, round, and complex shape. In step 840, target classifier 550 may detect an anatomical region of interest (e.g., a brain metastasis) based on the classified objects in the subset.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

The words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items. In addition, the singular forms "a," "an," and "the" are intended to include plural references, unless the context clearly dictates otherwise.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system for detecting an anatomical region of interest, comprising:
   a memory device storing computer-executable instructions; and
   at least one processor device communicatively coupled to the memory device, wherein the computer-executable instructions, when executed by the at least one processor device, cause the processor device to perform operations including:
      identifying a plurality of objects in a medical image;
      selecting a subset of the objects by applying a morphology filter to the plurality of objects, wherein the morphology filter determines a morphological feature associated with each of the plurality of objects and excludes at least one object from the subset when the morphological feature of the at least one object exceeds a predetermined threshold;
      classifying the objects in the subset into one of a predetermined set of shapes, wherein the predetermined set of shapes includes one or more of a point, a line, a round shape, and a complex shape; and
      detecting the anatomical region of interest based on the classified objects in the subset.

2. The system of claim 1, wherein the anatomical region of interest includes a brain metastasis.

3. The system of claim 1, wherein the morphological feature includes a depth of a convexity defect and the operations further comprise:
   determining the depth of the convexity defect based on a distance from the convexity defect to a convex hull enclosing a corresponding object.

4. The system of claim 3, wherein the object includes a plurality of convexity defects and the morphological feature includes the depth of a deepest convexity defect.

5. The system of claim 3, wherein the operations further comprise:
   determining the convexity defect based on a contour of the corresponding object.

6. The system of claim 1, wherein the operations further comprise:
   removing the at least one object excluded from the subset from the medical image.

7. The system of claim 1, wherein the operations further comprises:
removing one or more objects classified as a point or a line from the subset; and
detecting the anatomical region of interest based on the subset after removal of the one or more objects classified as a point or a line.

8. The system of claim 1, wherein the medical image includes a Magnetic Resonance Imaging (MRI) image.

9. The system of claim 1, wherein the medical image comprises a two-dimensional (2D) image.

10. The system of claim 9, wherein the medical image is a 2D slice of a three-dimensional (3D) image, the 3D image including a plurality of 2D slices, and wherein the operations further comprises:
selecting a respective subset of objects for each of multiple 2D slices by applying the morphology filter to each of the multiple 2D slices;
classifying the objects in the respective subset into one of the predetermined set of shapes; and
detecting the anatomical region of interest based on the classified objects in a collection of the subsets corresponding to the multiple 2D slices.

11. The system of claim 10, wherein the at least one processor device includes a plurality of computing cores, and wherein the operations further comprise:
executing, by each of the plurality of computing cores, application of the morphology filter to a separate 2D slice.

12. The system of claim 10, wherein the operations further comprises validating the classified objects in the collection of the subsets, including at least one of:
removing one or more objects classified as non-circular shapes from their respective subsets;
removing an object from its corresponding subset when the object is not adjacent to another object located in an adjacent 2D slice;
removing a pair of objects mirroring each other from their respective subsets; or
removing one or more objects located at a predetermined anatomical area from their respective subsets.

13. The system of claim 12, wherein the operations further comprise:
determining a confidence measure for each of the remaining objects in the collection of the subsets after the validation, where in the confidence measure indicates a likelihood that a particular object is the anatomical region of interest; and
dividing the remaining objects into a plurality of groups according to their respective confidence measures.

14. A method, implemented by at least one processor device executing computer-executable instructions, for detecting an anatomical region of interest, comprising:
identifying a plurality of objects in a medical image;
selecting a subset of the objects by applying a morphology filter to the plurality of objects, wherein the morphology filter determines a morphological feature associated with each of the plurality of objects and excludes at least one object from the subset when the morphological feature of the at least one object exceeds a predetermined threshold;
classifying the objects in the subset into one of a predetermined set of shapes, wherein the predetermined set of shapes includes one or more of a point, a line, a round shape, and a complex shape; and
detecting the anatomical region of interest based on the classified objects in the subset.

15. The method of claim 14, wherein the medical image includes a Magnetic Resonance Imaging (MRI) image.

16. The method of claim 14, wherein the anatomical region of interest includes a brain metastasis.

17. The method of claim 14, wherein the morphological feature includes a depth of a convexity defect and the method further comprises:
determining the depth of the convexity defect based on a distance from the convexity defect to a convex hull enclosing a corresponding object.

18. The method of claim 17, wherein the object includes a plurality of convexity defects and the morphological feature includes the depth of a deepest convexity defect.

19. The method of claim 17, further comprising:
determining the convexity defect based on a contour of the corresponding object.

20. The method of claim 14, further comprising:
removing the at least one object excluded from the subset from the medical image.

21. The method of claim 14, further comprising:
removing one or more objects classified as a point or a line from the subset; and
detecting the anatomical region of interest based on the subset after removal of the one or more objects classified as a point or a line.

22. The method of claim 14, wherein the medical image comprises a two-dimensional (2D) image.

23. The method of claim 22, wherein the medical image is a 2D slice of a three-dimensional (3D) image, the 3D image including a plurality of 2D slices, and the method further comprises:
selecting a respective subset of objects for each of multiple 2D slices by applying the morphology filter to each of the multiple 2D slices;
classifying the objects in the respective subset into one of the predetermined set of shapes; and
detecting the anatomical region of interest based on the classified objects in a collection of the subsets corresponding to the multiple 2D slices.

24. The method of claim 23, further comprising validating the classified objects in the collection of the subsets, including at least one of:
removing one or more objects classified as non-circular shapes from their respective subsets;
removing an object from its corresponding subset when the object is not adjacent to another object located in an adjacent 2D slice;
removing a pair of objects mirroring each other from their respective subsets; or
removing one or more objects located at a predetermined anatomical area from their respective subsets.

25. The method of claim 24, further comprising:
determining a confidence measure for each of the remaining objects in the collection of the subsets after the validation, where in the confidence measure indicates a likelihood that a particular object is the anatomical region of interest; and
dividing the remaining objects into a plurality of groups according to their respective confidence measures.

26. The method of claim 23, wherein the at least one processor device includes a plurality of computing cores, and the method further comprises:
executing, by each of the plurality of computing cores, application of the morphology filter to a separate 2D slice.

27. A non-transitory computer-readable medium that stores a set of instructions that is executable by at least one processor of a device to cause the device to perform a method for detecting an anatomical region of interest, the method comprising:

identifying a plurality of objects in a medical image;

selecting a subset of the objects by applying a morphology filter to the plurality of objects, wherein the morphology filter determines a morphological feature associated with each of the plurality of objects and excludes at least one object from the subset when the morphological feature of the at least one object exceeds a predetermined threshold;

classifying the objects in the subset into one of a predetermined set of shapes, wherein the predetermined set of shapes includes one or more of a point, a line, a round shape, and a complex shape; and detecting the anatomical region of interest based on the classified objects in the subset.

* * * * *